United States Patent
Royster, Jr. et al.

[11] Patent Number: 5,856,079
[45] Date of Patent: Jan. 5, 1999

[54] PREPARATION AND USE OF A DIMETHYLAMINE SILVER BROMO-IODIDE COMPLEX AS A SINGLE SOURCE PRECURSOR FOR IODIDE INCORPORATION IN SILVER BROMIDE CRYSTALS

[75] Inventors: Tommie L. Royster, Jr.; Seshadri Jagannathan, both of Rochester; David E. Fenton, Fairport; Samuel Chen, Penfield, all of N.Y.

[73] Assignee: Eastman Kodak Company, Rochester, N.Y.

[21] Appl. No.: 865,753

[22] Filed: May 30, 1997

[51] Int. Cl.$^6$ .............................. G03C 1/005; C01G 5/00; C01G 5/02; C07F 1/10
[52] U.S. Cl. .............................. 430/569; 423/23; 423/42; 117/938; 205/507; 556/110
[58] Field of Search .............................. 430/569; 423/23, 423/42; 117/938; 205/507; 556/110

[56] References Cited

U.S. PATENT DOCUMENTS

| | | | |
|---|---|---|---|
| 3,883,355 | 5/1975 | Walworth | 430/569 |
| 3,941,600 | 3/1976 | Walworth | 430/569 |
| 4,153,462 | 5/1979 | Gerber et al. | 430/569 |
| 4,340,666 | 7/1982 | Walworth | 430/569 |
| 5,147,771 | 9/1992 | Tsaur et al. | 430/569 |
| 5,478,718 | 12/1995 | Verbeeck et al. | 430/569 |
| 5,541,051 | 7/1996 | Verbeeck et al. | 430/569 |
| 5,604,087 | 2/1997 | Lapp et al. | 430/569 |
| 5,759,762 | 6/1998 | Budz et al. | 430/611 |

OTHER PUBLICATIONS

Beilstein Database, Beilstein Reg. No. 4921664, Mar. 1998.

*Primary Examiner*—Mark P. Huff
*Attorney, Agent, or Firm*—Arthur H. Rosenstein

[57] ABSTRACT

A dimeitylarnine silver bromo-iodide complex is used as a single source precursor for iodide incorporation in silver bromide crystals.

8 Claims, No Drawings

PREPARATION AND USE OF A DIMETHYLAMINE SILVER BROMO-IODIDE COMPLEX AS A SINGLE SOURCE PRECURSOR FOR IODIDE INCORPORATION IN SILVER BROMIDE CRYSTALS

FIELD OF THE INVENTION

This invention relates to the process of iodide incorporation in silver bromide crystals. In particular, it relates to the use of a unique silver halide complex contained in a dimethylamine solution that can be used as single source material for iodide incorporation in silver bromide crystals.

BACKGROUND OF THE INVENTION

Silver halide emulsions are generally prepared using a reactive precipitation process; aqueous solutions of silver nitrate and alkali halides are reacted in the presence of gelatin. The composition of resultant product (silver halide emulsions) is tuned by varying the constituents of the alkali halide solution. For example, the precipitation of pure silver bromide emulsions is carried out using sodium bromide as the alkali halide, while silver bromide emulsions are precipitated using sodium bromide as the alkali halide. Appropriate addenda/dopants are generally introduced as aqueous solutions during the precipitation process, to generate silver halide emulsions of desired composition.

The important feature of all these processes is the bimolecular chemical reaction between (Ag+) ions and the appropriate anion(s) to generate the precipitating species. It is possible to vary the chemical and the structural composition of the product emulsion by varying the constituents of the reagent solutions, but the chemical reaction responsible for the generation of the desired silver halide emulsion is always the reaction between (Ag+) ions that are present in a solution or on the surface of the silver halide emulsion, and the appropriate anion(s).

From an operational point of view, generation of silver halide emulsions by this reactive precipitation process involves the addition of concentrated reagent solutions into a reactor under vigorous mixing conditions. The goal of the mixing process is to minimize the volume of the reactor that is exposed to the unreacted reagent solutions. However, even under ideal mixing conditions, the volume of the reactor that is exposed to the unreacted reagents is finite and relatively large.

In order to understand the reasons for the exposure of the reactor contents to unreacted reagents it is necessary to examine the mechanism of the mixing process. Mixing in emulsion precipitation processes is achieved by means of a rapidly spinning rotary agitator. The momentum generated by the rotary agitator results in the circulation of the fluid in the reactor. Appropriate baffling devices are used to randomize the fluid motion in the reactor, to achieve efficient mixing. It is important to recognize that efficient mixing requires rapid circulation of the fluid in thereafter. In a typical emulsion generation process, the reagent solutions are introduced into a region of the reactor that experiences good mixing. Consequently, the concentrated reagent solutions are introduced into a region of the reactor that experiences rapid circulation of the fluid in the reactor; i.e. the reagent introduction region in the reactor is exposed frequently to the contents of the reactor.

It is also important to recognize that efficient mixing is necessary at the reagent introduction region, in order to promote the reaction between the concentrated reagents. Because this (efficient) mixing process is carried out by rapid circulation of the reactor fluid through the reagent introduction region, the contents of the reactor are necessarily exposed to the concentrated reagents. From a kinetic view point, the extent of exposure of the reactor contents to the unreacted reagents would depend on the rate of dilution of the concentrated reagents relative to the rate of the chemical reaction between the concentrated reagents. Under ideal mixing conditions, the rate of dilution of the concentrated reagents is determined by the molecular/ionic diffusivity of the reactant species; which is still considerably smaller than the rate of the relevant chemical reactions. Hence, the extent of exposure of the reactor contents to the unreacted reagents can be significant even under ideal mixing conditions.

The unintentional exposure of the reactor contents to the unreacted reagents can have undesired effects on the emulsion crystals. For example, exposure of emulsion crystals to unreacted silver nitrate can result in the creation of fog centers in the crystals, while exposure of emulsion crystals to unreacted concentrated, potassium iodide can result in the destruction of grains. The grain destruction can be avoided by using dilute solutions of potassium iodide, solutions of iodide that also contain sodium bromide and long addition times. The disadvantages of this approach is the large volume of the reagents and the extension of the precipitation time (yield and productivity).

An alternative to the above approach is the use of silver iodide dissolved in an appropriate solvent as the source of iodide.

Halide introduction from concentrated solutions of silver halide complexes prepared from methylamineformamide and excess halide have been reported. However, methylamineformamide is exceedingly hazardous and the solvent has been documented as a teratogen (promotes deformity in embryos).

SUMMARY OF THE INVENTION

This invention addresses the limitations of the prior art for iodide incorporation in silver bromide crystals. A solution or low melting point solid of hydrated dimethylamine hydrobromide ([Me$_2$NH$_2$]Br) containing the silver iodide precursor complex [Me$_2$NH$_2$]$_n$[AgIBr$_n$], wherein n is 1 to 5, is disclosed as a single source material for the incorporation of iodide into silver bromide crystals. Iodide incorporation is accomplished by introducing the precursor material to an aqueous medium of silver bromide crystals. Under aqueous conditions, iodide is released from the complex as silver iodide which eliminates the problems of free iodide supersaturation that results in destruction of silver bromide crystals. This process also provides kinetic control for releasing the silver iodide promoting homogeneous incorporation.

DETAILED DESCRIPTION OF THE PREFERRED EMBODIMENTS

This invention relates to the preparation of a silver bromo-iodide complex as a precursor to the formation of silver iodide for incorporation in silver bromide crystals. The complex [Me$_2$NH$_2$]$_n$[AgIBr$_n$] contained in solid or liquid hydrated [Me$_2$NH$_2$]Br provides a single source material for silver iodide precipitation. Preparation of the material can be accomplished by combining silver iodide with hydrated [Me$_2$NH$_2$]Br or dissolving the isolated complex [Me$_2$NH$_2$][AgIBr] in the hydrated salt.

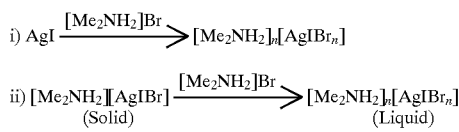

This invention uses the materials prepared by the preceeding process to incorporate silver iodide into silver bromide crystals. Iodide incorporation is accomplished by introducing hydrated [Me$_2$NH$_2$]Br that contains the precursor complex into an aqueous medium of silver bromide crystals. Under these conditions iodide is precipitated as silver iodide.

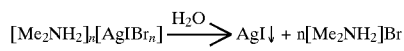

Thus, an amine salt [(CH$_3$)$_2$NH$_2$]Br can be hydrated with water and silver iodide can be introduced to form [Me$_2$NH$_2$]$_n$[AgIBr$_n$] or the amine salt can be combined with silver iodide in a dimethylformamide (DMF) solvent and heated to form crystals of the complex [(CH$_3$)$_2$NH$_2$][AgIBr] which are dissolved in hydrated [Me$_2$NH$_2$]Br. Alternatively, concentrated HBr can be substituted for [(CH$_3$)$_2$NH$_2$]Br as the bromide source. The silver halide crystals involved are prepared using [(CH$_3$)$_2$NH$_2$]$_n$[AgIBr$_n$] as the source of iodide to form silver bromo-iodide crystals.

The following are examples of the invention.

EXAMPLE 1

Method A

The amine salt [Me$_2$NH$_2$]Br was initially hydrated by using a stoichiometric amount of water (the water/amine mol ratio ranged from 1–2). Then, silver iodide was introduced (the amine/silver mol ratio was $\geq 13$) followed by heating the mixture to steambath temperature. When a clear colorless solution was observed, the material was removed from the heat and allowed to cool to room temperature.

Method B

The amine salt [Me$_2$NH$_2$]Br was combined with silver iodide using a molar ratio of 1:1 in DMF solvent (an equivalent amount of concentration can be substituted for [Me$_2$NH$_2$]Br). The mixture was then heated to steambath temperature until a clear colorless solution was observed. After cooling to room temperature, the solution was layered with diethyl ether and allowed to stand for 16 h. Crystals of the complex [Me$_2$NH$_2$][AgIBr] were isolated after decanting or filtering the solution followed by washing the material with diethyl ether. The isolated complex was then dissolved in the hydrated [Me$_2$NH$_2$]Br solvent.

The advantages of this chemistry are illustrated with the following examples.

EXAMPLE 2

Substrate

A monodisperse AgBr tabular emulsion was prepared according to the general procedure described in U.S. Pat. No. 5,147,771 and was used as the common substrate in all the examples. This emulsion was characterized to be 2.18 microns in diameter and 0.118 microns in thickness.

EXAMPLE 3

Step 1: In a 6 liter reactor, ca. 1.5 moles of the emulsion from example 2 containing ca. 40 g/mole of gelatin was mixed with 3 liters of water maintained at 60° C. The pH of the mixture was adjusted to 1.21 and the pAg to 7.56.

Step 2: 201.83 g of an aqueous solution containing 7.12 g of KI and 73.57 g of NaBr was added rapidly to the emulsion from step 1 and the resulting emulsion was agitated for 10 minutes.

Step 3: 397.8 cc of 1.6M silver nitrate solution was added to emulsion obtained from step 2 over a period of 5.83 minutes.

Step 4: The emulsion obtained from step 3 was washed and the final pH was adjusted to 5.5/40° C. and the pAg to 8.23/40° C.

Step 5: The emulsion obtained from step 4 was characterized to be 3.34 microns in diameter and 0.158 microns in thickness.

Step 6: This emulsion was then characterized by transmission electron microscopy, and also evaluated for photographic performance.

EXAMPLE 4

Step 1: Same as example 3.

Step 2: 90.38 g of solution containing 70.30 g of dimethylamine hydrobromide, 10.07 g of silver iodide powder and 10.01 g of deionized water was added to the emulsion obtained from step 1.

Step 3: Same as example 3.

Step 4: Same as example 3.

Step 5: The emulsion obtained from step 4 was characterized to be 3.39 microns in diameter and 0.157 microns in thickness.

Step 6: This emulsion was then characterized by transmission electron microscopy, and also evaluated for photographic performance.

Emulsion Grain Morphology and Composition Evaluation

Both example 1 and example 2 were analyzed by transmission electron microscopy/analytical electron microscopy to determine their grain population distribution. In these emulsions, four types of grains are discernible:

Type 1) These T-grains contain greater than three dislocation lines, primarily in the outer perimeter regions (and confined mostly to the corner regions). These grains contain about 3 mole % iodide as measured at the end of emulsion precipitation.

Type 2) These are similar to type (1)grains, but in addition, they have greater than three dislocation lines visible over central (111) tabular face region. These grains contains about 3–6 mole % iodide.

Type 3) These are tabular grains with observable portions of the grain missing. These grains contain high levels of iodide (typically 12–18 mole %).

Type 4) These grains contain $\leq 3$ dislocation lines (either in the perimeter or over the central tabular face region), and have very low iodide concentrations (<1 mole %).

Table 1 shows the results of Examples 3 and 4.

TABLE 1

| TEM Analysis of Grain Population Distribution | | |
|---|---|---|
| Emulsion | Example 3 | Example 4 |
| Iodide Source | KI | [ME$_2$NH$_2$][AgIBr$_n$] |
| Type 1 | 85.9% | 90.8% |
| Type 2 | 0.4% | 2.59% |
| Type 3 | 3.09% | 2.2% |
| Type 4 | 10.6% | 4.5% |
| Grains counted | 263 | 315 |

Photographic Evaluation

Emulsions described in Examples 3 and 4 above were chemically and spectrally sensitized in a finish factorial experiment using a green sensitizing dye, Benzoxazolium, 5-chloro-2-(2-((5-phenyl-3-(3-sulfobutyl)-2(3H)-benzoxazolylidene) methyl)-1-butenyl)-3-(3-sulfopropyl)-, inner salt, compound with N, N-diethylethanamine (1:1). The sensitized emulsions were combined with a cyan-dye forming coupler, Hexanamide, 2-(2,4-bis(1,1-dimethylpropyl)phenoxy)-N-(4-((((4-cyanophenyl) amino) carbonyl)amino)-3-hydroxyphenyl)- and coated on a photographic film support with a silver coverage of 807 mg/m$^2$ (75 mg/ft$^2$) and a coupler laydown at double that. A sample of each coating was exposed with a tungsten light source for 1/50th second through a Wratten 9 filter. Exposed film samples were developed for 3 minutes and 15 seconds using Kodak Flexicolor C-41 color negative processing. Speed is reported in relative log speed units. Each unit difference in relative speed represents 0.01 log E, where E represents speed in lux-seconds. Speed was measured at a density of 0.15 above fog.

Optimal sensitization levels were somewhat different for the two emulsions though both emulsions required identical levels of sensitizing dye. Sensitometry for the optimally finished emulsions is indicated on Table 2.

TABLE 2

| Sensitometric Comparison, Relative Speeds | | | |
|---|---|---|---|
| | Dmin | 0.15 D Speed | Maximum Slope |
| Example 3 | 0.127 | 100 | 1.78 |
| Example 4 | 0.081 | 102 | 1.90 |

As can be seen from the table, Example 2 provides slightly higher speed at higher slope and lower Dmin.

The advantages of this invention are that it provides a novel process for incorporating iodide in silver bromide emulsions in a controlled manner, under low super-saturation conditions, it allows for better utilization of preferred locations on the substrate emulsion for the incorporation of iodide and dislocations, dislocations can be generated in a controlled manner in silver bromide emulsions, under low super-saturation conditions, it minimizes batch to batch and scale to scale variability, and it improves scalability.

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

We claim:

1. A method of preparing a solution of a dimethylamine silver bromo-iodide complex [(CH$_3$)$_2$NH$_2$]$_n$[AgIBr$_n$] in water wherein n=1 to 4 comprising reacting AgI with [(CH$_3$)$_2$NH$_2$]Br and water.

2. The method of preparing [(CH$_3$)$_2$NH$_2$][AgIBr] comprising adding [(CH$_3$)$_2$NH$_2$]Br to AgI in the presence of dimethylformamide.

3. The method of preparing [Me$_2$NH$_2$][AgIBr] comprising adding concentrated HBr to AgI in the presence of dimethylformamide.

4. The method of preparing a solution of a dimethylamine silver bromo-iodide complex [(CH$_3$)$_2$NH$_2$]$_n$[AgIBr$_n$] comprising dissolving [(CH$_3$)$_2$NH$_2$][AgIBr] in [(CH$_3$)$_2$NH$_2$]Br and water.

5. A method of precipitating silver iodide comprising introducing a solution containing the single source precursor [(CH$_3$)$_2$NH$_2$]$_n$[AgIBr]$_n$ in water wherein AgI precipitates out leaving in [Me$_2$NH$_2$]Br wherein n is 1 to 5.

6. A method of incorporating iodide into silver bromide crystals comprising adding [(CH$_3$)$_2$NH$_2$]$_n$[AgIBr$_n$] into a silver bromide emulsion wherein n is 1 to 5.

7. A method of incorporating iodide into silver bromo-iodide crystals comprising adding [(CH$_3$)$_2$NH$_2$]$_n$[AgIBr$_n$] in solution with water wherein n is 1 to 5 into a silver bromo-iodide emulsion.

8. An isolated crystal of a complex having the structure: [(CH$_3$)$_2$NH$_2$][AgIBr].

* * * * *